United States Patent [19]

Nohl et al.

[11] Patent Number: 4,891,137

[45] Date of Patent: Jan. 2, 1990

[54] METHOD AND APPARATUS FOR MEMBRANE EXTRACTION OF HYDROLYSIS CONTAMINATES

[75] Inventors: Andre Nohl, San Jose; Ronald V. Perkins, Union City, both of Calif.

[73] Assignee: Spectra-Physics, Inc., San Jose, Calif.

[21] Appl. No.: 319,208

[22] Filed: Mar. 3, 1989

[51] Int. Cl.$^4$ ............................................. B01D 13/00
[52] U.S. Cl. ................................... 210/644; 210/656; 210/500.23
[58] Field of Search ................... 210/644, 500.23, 634, 210/638, 656; 530/330, 309, 329, 334

[56] References Cited

U.S. PATENT DOCUMENTS 3,951,789  4/1976  Lee et al. ............................ 210/644

Primary Examiner—Frank Spear
Attorney, Agent, or Firm—Skjerven, Morrill, MacPherson, Franklin & Friel

[57] ABSTRACT

A process removes FMOC—OH which is an undesirable by-product of the derivatization of amino acids by FMOC. The process uses a silicone rubber membrane extractor cell. The sample containing the FMOC—OH is held in a silicone rubber tubing, while pentane flows past the outside of the tube; the FMOC—OH is thus extracted from the sample into the pentane. The process is integrated into a conventional high performance liquid chromatography system and is readily automated.

10 Claims, 4 Drawing Sheets

METHOD AND APPARATUS FOR MEMBRANE EXTRACTION OF HYDROLYSIS CONTAMINATES

BACKGROUND OF THE INVENTION

1. Field of the Invention

This invention relates to a chemical process and apparatus involving amino acid derivatization with FMOC using a silicone membrane to extract an undesirable hydrolysis product from the amino acid sample.

2. Description of the Prior Art

Derivatization of amino acids with FMOC is a well known process. FMOC is an abbreviation for 9-fluorenylmethyl chloroformate. This derivatization is performed on a sample prior to testing the sample for amino acids, for instance testing by liquid chromatography to determine exactly what amino acids are present in a sample. This derivatization, i.e., mixing an FMOC solution with an amino acid sample, produces a hydrolysis product called FMOC—OH, which interferes with the peaks of interest in the liquid chromatography process. That is, the derivatization process creates a "ghost peak" in the chromatogram because of the undesirable presence of FMOC—OH in the sample.

FIG. 1 shows the position of the ghost peak 1 caused by FMOC—OH in a conventional chromatogram, with the genuine peaks 2A, ..., 2G caused by amino acids labeled with the names of the various amino acids. Peak 1 is a ghost because it is not an amino acid peak, but is a by-product of the derivatization reaction, and masks or interferes with important data (i.e., other peaks) in the amino acid analysis. The FMOC derivatization is otherwise a useful process because it is a very sensitive, quick reaction and does not require heating.

A method called liquid-liquid extraction to remove the FMOC—OH contaminant from a sample before testing has been developed in the prior art. In the prior art, the FMOC derivatization process thus includes these steps:

1. Place a sample of amino acid and a quantity of FMOC in a vial and mix.
2. Add pentane (a well known liquid hydrocarbon, $C_5H_{12}$).
3. Mix (i.e., shake the vial) and wait for the mixture to separate into two layers.
4. Pour off the pentane (which is the top layer in the vial) from the lower aqueous layer.
5. Repeat steps 2, 3 and 4 several times.

This process removes most of the FMOC—OH, which is extracted by the pentane. This mixing with pentane and layering is called liquid-liquid extraction, and typically removes about 70% to 80% of the FMOC—OH, usually enough to eliminate interferences from the ghost peak when the derivatized amino acid sample is subjected to liquid chromatography.

FIG. 2 shows the result of a prior art manual pentane extraction, showing a chromatogram with an FMOC—OH peak 1 and a valine amino acid peak 2D, where two extractions were performed. The FMOC—OH peak 1 is 6% of the total peak area. This prior art process has the significant disadvantage that it is a manual method, requiring a skillful technician to observe and pour off the pentane layer.

The prior art process thus has the disadvantages that it is a manual method, and cannot be automated due to the need for visual observation and layer separation; and it is very time consuming (and hence impractical) to prform many extractions, and hence a significant proportion of FMOC—OH is not extracted.

Also well known, but not in connection with amino acid derivatization using FMOC, is membrane extraction. Membrane extraction is known for purposes of extracting trace organic compounds from aqueous samples. Typical of the organic compounds extracted are phenols, caffeine, phenylephrine hydrochloride, and various esters.

R. G. Melcher describes a membrane/flow injection system in "Flow-Injection Determination of Membrane-Selected Organic Compounds", *Analytica Chemica Acta* 214 (1988) pg. 299-313. Melcher discloses the process of membrane extraction with a continuous (nonporous membrane) such as a silicone rubber membrane. First, an aqueous sample is brought into contact with one surface of the membrane and some of the material to be analyzed is absorbed by the membrane. Second, the material absorbed into the membrane diffuses through the membrane to the second surface of the membrane. Third, some of the material is removed from the membrane by an extracting solution (an extractant) on the second surface of the membrane.

In a dynamic system a constant flow of the sample is maintained on one surface of the membrane and a constant flow of the extracting is maintained on the second surface.

FIG. 3 shows a membrane/flow-injection system as disclosed by Melcher for use in extracting organic compounds such as phenols from an aqueous sample. Shown in FIG. 3 are the extractant reservoir 4, extractant pump 5, membrane 6A in cell 6, detector 8, data recorder 10, carrier (i.e., solvent for the sample) reservoir 12, carrier pump 14, sample inlet 16, six port valve 18, and sample loop 18L in valve 18. Detector 8 is a conventional liquid chromatography detector. The membrane 6A used in cell 6 is silicone rubber tubing. Six port valve 18 is a conventional six port rotary injection valve. The system as shown in FIG. 3 is readily automated. It is typically used for extracting trace amounts of compounds from aqueous samples, so that the extracted compounds (not the aqueous sample) can be subject to testing.

SUMMARY OF THE INVENTION

In accordance with the invention, a silicone-rubber membrane and an extractant including pentane are used to extract FMOC—OH from the derivatization of amino acids using FMOC. A derivatized sample is placed on one side of the silicone rubber membrane, while the extractant (pentane) is flushed past the second side of the membrane. Extraction of the FMOC—OH occurs through the membrane.

Because there is thus no need to separate two layers, the invention has the advantage that it is not a batch process. Since fresh pentane is continuously flowing past the membrane, nearly 100% extraction of FMOC—OH is possible. The process of the present invention can be automated in a flow stream system, unlike the prior art manual process which requires visual observation of the two layers.

Preferably the membrane of the invention is a tube. A flat membrane or other membrane configuration can also be used. Materials other than silicone rubber such as a conventional commercially available teflon membrane material can be used for the membrane in another embodiment of the invention.

BRIEF DESCRIPTION OF THE DRAWINGS

Identical reference numbers in various figures denote identical or similar structures.

DETAILED DESCRIPTION OF THE INVENTION

Figure 4:
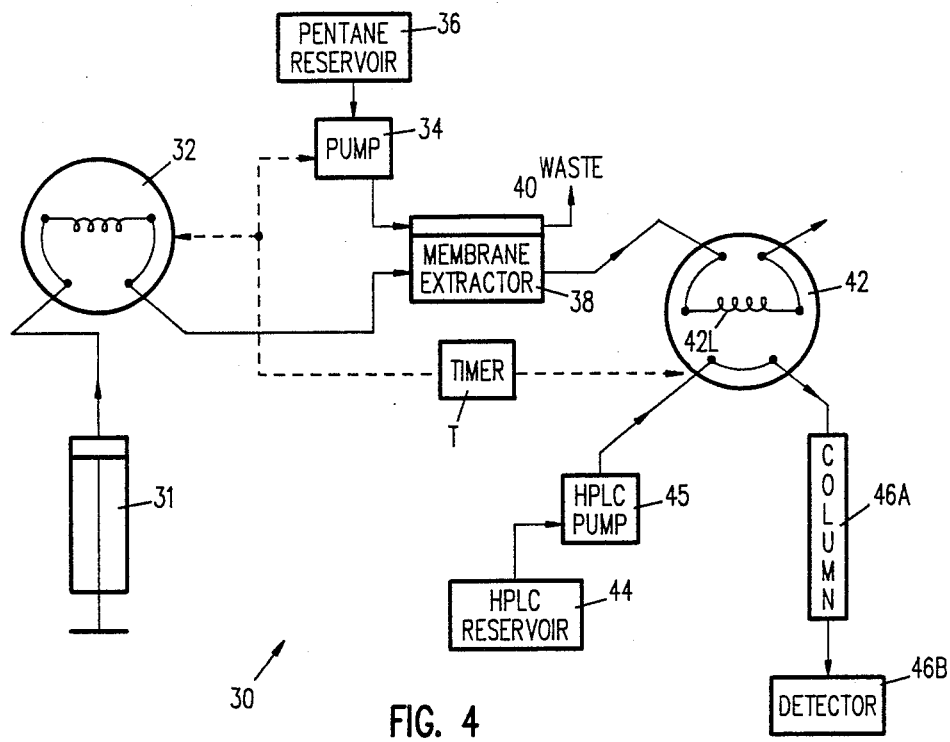
FIG. 4 shows a membrane extraction system in accordance with the present invention.

In accordance with the preferred embodiment of the invention, a high performance liquid chromatography (HPLC) system 30 as shown in FIG. 4 is used. The system 30 includes syringe 31 for pushing a quantity of a liquid sample including amino acids (typically 1.5 $\mu$gram/ml concentration) into a first conventional multiport sample loading valve 32. Sample loading valve 32 is connected to the membrane extractor 38. Membrane extractor 38 is also connected to pentane pump 34, which pumps fresh liquid pentane from pentane reservoir 36 into membrane extractor 38.

The pentane is circulated from pentane reservoir 36 through pump 34 through membrane extractor 38 and to waste 40. The sample passes through membrane extractor 38, at which stage the FMOC—OH is removed, and the sample passes into a conventional six port rotary injection valve 42 which includes sample loop 42L. At rotary injection valve 42 a quantity of solvent (also conventionally called "the mobile phase") provided from reservoir 44 by HPLC pump 45 is mixed with the sample, and the resulting mixture passes into the detector 46 when valve 42 is thrown.

Detector 46 includes a conventional HPLC column 46A and fluorescent detector 46B which are described in more detail below.

Figure 5A:
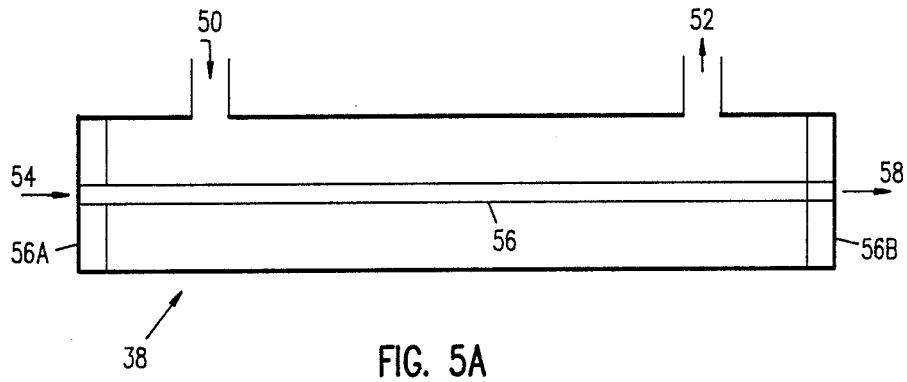
FIGS. 5A and 5B show membrane extractor cells in accordance with the present invention.

Membrane extractor 38 in accordance with the preferred embodiment of the invention is as shown in FIG. 5A. Pentane from pentane pump 34 (see FIG. 4) enters extractant inlet 50 and circulates through the extractor to extractant outlet 52 to waste 40 (see FIG. 4). The sample enters sample inlet 54 and flows through membrane tubing 56 to sample outlet 58, and to rotary valve 42 (not shown, see FIG. 4). Membrane tubing 56 is preferably conventional medical-grade silicone rubber tubing about 0.1 to 0.2 mm in wall thickness, as commercially available from Dow Corning under the name "Silastic". The tubing 56 is preferably 0.5 mm to 1.2 mm outside diameter, and a piece of tubing preferably about 60 to 100 mm in length is used in membrane extractor 38. The tubing dimensions are not critical to the invention.

Membrane extractor 38 in the preferred embodiment of the invention is similar in structure to a conventional laboratory condenser, except that the inner glass tube normally present in such a condenser is replaced by the silicon rubber tubing 56.

In the preferred embodiment (see FIG. 5A), the flow rate of pentane through membrane extractor 38 is about 0.1–1 ml/minute. The body 58 of membrane extractor 38 is preferably glass tubing about 1 to 2 mm in inside diameter. Membrane tubing 56 is connected at both ends 56A, 56B to membrane extractor body 58 by conventional means (i.e., preferably conventional push-on barbed fittings).

Figure 5B:
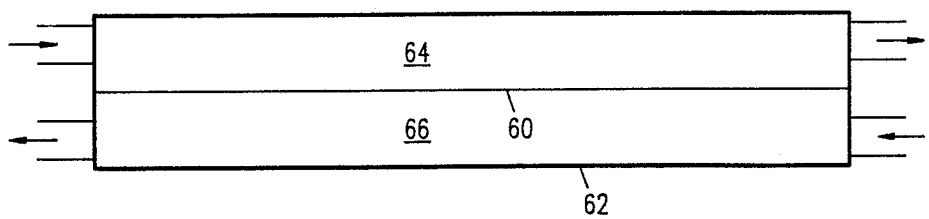

Other embodiments of the invention use other types of membrane extractor cells, as are known in the art. One other embodiment uses a flat membrane 60, preferably of 0.005 inch 0.127 mm) or less thickness as shown in FIG. 5B. Here membrane 60 is stretched across membrane extractor body 62, dividing the body 62 into two chambers 64, 66. Pentane flows through chamber 64, and the sample flows through chamber 66; the two flows are preferably in opposite directions as shown by the arrows. The dimensions of extractor body 62 are a matter of choice. Chambers 64, 66 are each preferably formed in a separate block of inert plastic, with serpentine channels (not shown) conventionally formed in each block to carry the flows of pentane and sample. The serpentine channels are preferably about 0.020 inches (0.51 mm) wide and about 0.030 inches (0.76 mm) deep.

In acccordance with the invention, the system 30 (see FIG. 4) operates as follows.

The amino acid sample and a desired quantity of FMOC are injected into the sample loading valve 32 by syringe 31. Then by means of syringe 31, about 100 $\mu$l or other convenient quantity of the mixture (containing the derivatized amino acids and FMOC—OH) are injected into membrane extractor 38. At this point, the mixture is held in the tubing 56 (see FIG. 5A) in membrane extractor 38, and pentane is pumped by pump 34 through membrane extractor 38. The pentane pumping continues, at about 0.1 to 1 ml/minute, preferably for about ten minutes to thirty minutes; a longer period of pentane pumping extracts more of the FMOC—OH.

Then the sample is pushed by syringe 31 out of membrane extractor 38 and into an HPLC injection valve 42, where about 20 $\mu$l of the sample is loaded into loop 42L. Conventional HPLC pump 45 then pumps the mobile phase solvent from reservoir 44 so as to push the sample from loop 42L into column 46A as described below. The preferred mobile phase solvent is a mixture of ACN (acetonitrite), MeOH (methanol), 0.3% acetic acid and 0.1% TEA (tri-ethylamine), the solvent having an adjusted pH of −4.2. When valve 42 is thrown, about 20 $\mu$l of sample in the pumped mobile phase solvent passes into a conventional detector 46, which preferably includes a 4.6×100 mm RP-14 18 3 $\mu$m column 46A and a conventional HPLC detector 46B using fluorescence detection at 254 nm eX (excitation wavelength) and 400–700 nm em (emission wavelength).

Figure 1:
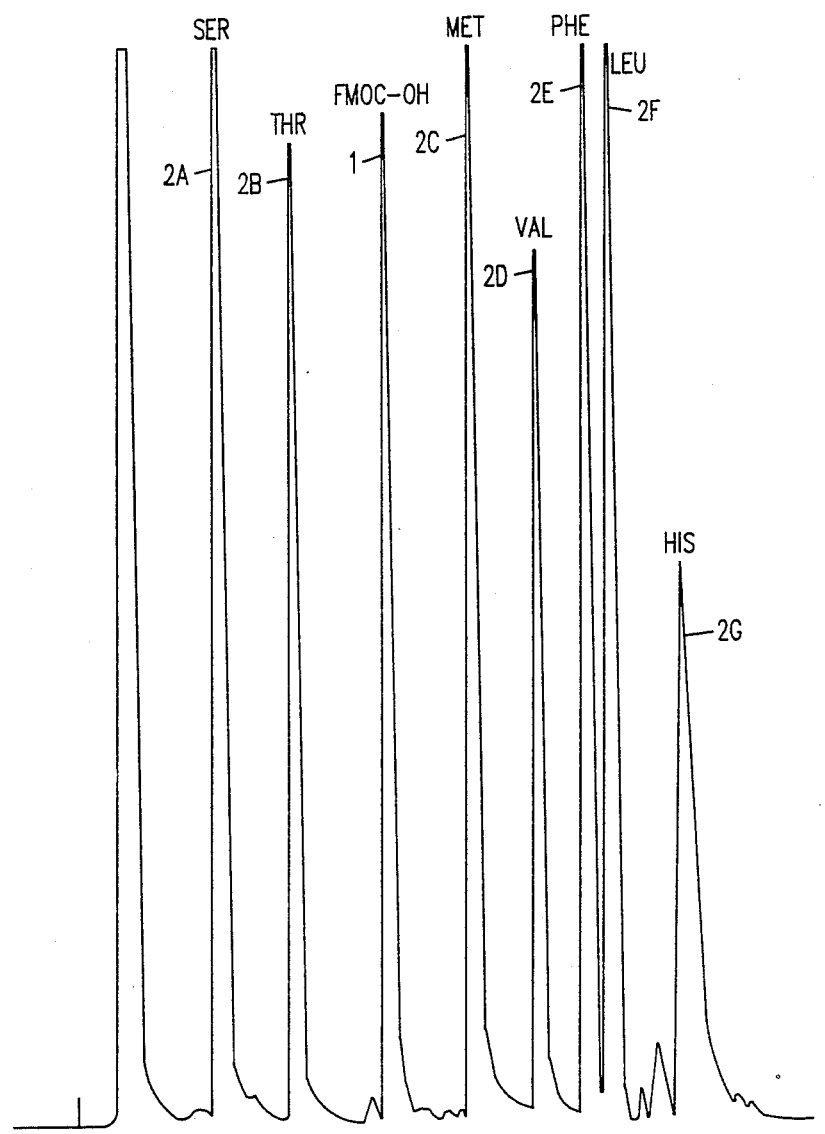
FIG. 1 shows the FMOC—OH "ghost peak".
Figure 2:
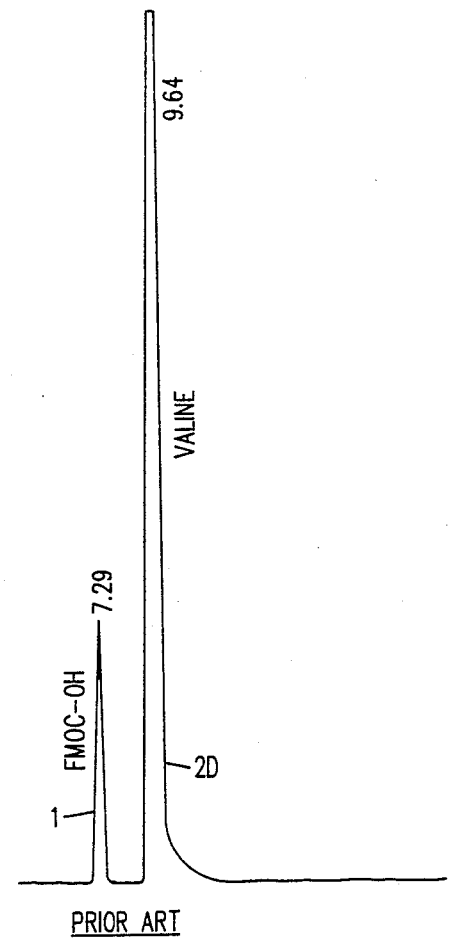
FIG. 2 shows the results of a prior art manual FMOC—OH extraction.
Figure 3:
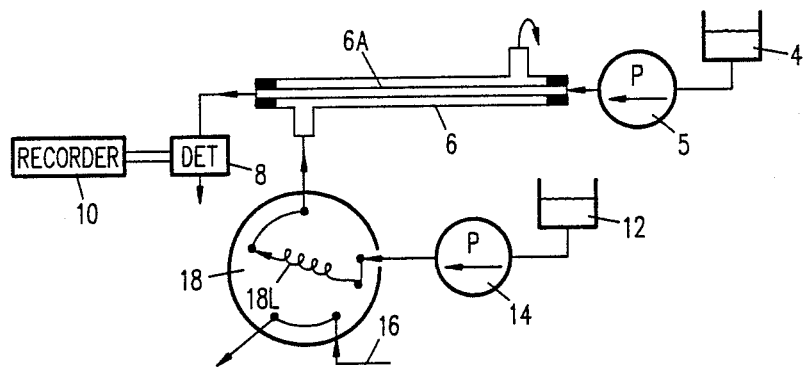
FIG. 3 shows a prior art membrane extraction system.
Figure 6:
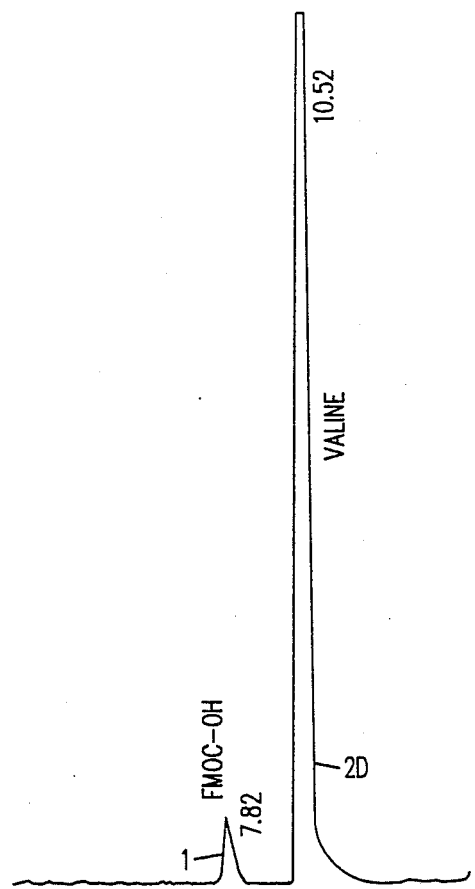
FIG. 6 shows results of an extraction performed in accordance with the present invention.

FIG. 6 shows a chromatogram resulting from an FMOC—OH extraction in accordance with the invention. In this chromatogram, the FMOC—OH peak 1 is less than 1% of the area of the valine amino acid peak 2D, where the extraction (i.e., pentane flow) lasted 30 minutes. Comparing FIG. 6 with the prior art of FIG. 2, where the FMOC—OH peak 1 is 6% of the total peak area, shows the superior extraction performed by the present invention.

Figure 7:
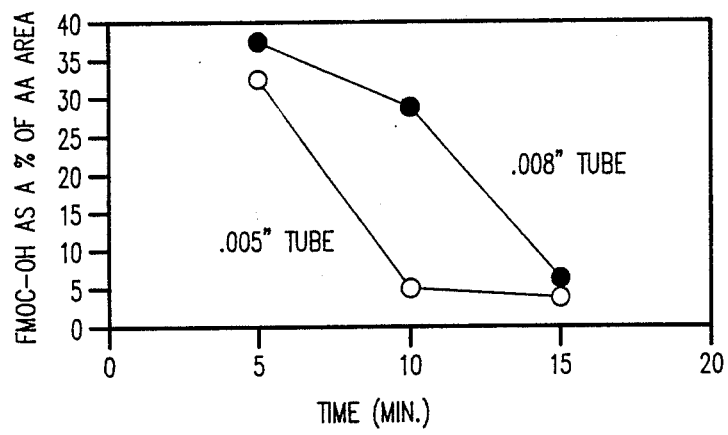
FIG. 7 shows the relation between extraction time and extraction effectiveness for two embodiments of the present invention.

FIG. 7 shows how, using the present invention, the FMOC—OH peak area (vertical scale) is a function of extraction time (horizontal scale) for two different membrane extractor tubings, one having a wall thickness of 0.005" (0.127 mm) and the second tubing having a wall thickness of 0.008" (0.2 mm).

In one embodiment, the system 30 of FIG. 4 is readily automated by conventionally providing a timer T to control the operation of sample loading valve 32, pentane pump 36, and injection valve 42 (each of which components includes a conventional electro-mechanical actuator, not shown), so as to provide an extraction period of a desired time during which the sample is present in membrane extractor 38 and is subject to the pentane flow. Timer T is preferably a conventional computer programmable timer, or alternatively is a conventional electromechanical or electrical timer.

The above description of the invention is illustrative and not limiting; other embodiments of the invention will be apparent in the light of the teachings of the invention.

We claim:

1. A method for extracting FMOC—OH from a sample comprising the steps of:
    providing an FMOC—OH permeable membrane having first and second sides;
    providing a sample contacting the first side; and
    providing an extractant including pentane on the second side.
2. The method of claim 1, further comprising the step of flowing the extractant past the second side.
3. The method of claim 2, further comprising the step, after the step of flowing the extractant, of injecting the sample into a liquid chromatography column.
4. The method of claim 1, wherein the step of providing the sample comprises mixing at least one amino acid with FMOC.
5. The method of claim 2, wherein the step of flowing the extractant is under automated control.
6. The method of claim 1, wherein the membrane comprises a silicone rubber membrane.
7. The method of claim 6, wherein the membrane further comprises tubing.
8. The method of claim 7, wherein the first side of the membrane is the inside of the tubing, and the second side of the membrane is the outside of the tubing.
9. The method of claim 6, wherein the membrane further comprises a flat sheet.
10. The method of claim 6, wherein the membrane is housed in a membrane extractor cell.

* * * * *